(12) United States Patent
Wanda (10) Patent No.: US 9,202,124 B2
(45) Date of Patent: Dec. 1, 2015

(54) IMAGE INFORMATION ACQUIRING APPARATUS, IMAGE INFORMATION ACQUIRING METHOD AND IMAGE INFORMATION ACQUIRING PROGRAM

(75) Inventor: Koichiro Wanda, Yokohama (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 71 days.

(21) Appl. No.: 13/810,423

(22) PCT Filed: Jul. 8, 2011

(86) PCT No.: PCT/JP2011/003919
§ 371 (c)(1),
(2), (4) Date: Jan. 15, 2013

(87) PCT Pub. No.: WO2012/011242
PCT Pub. Date: Jan. 26, 2012

(65) Prior Publication Data
US 2013/0114859 A1   May 9, 2013

(30) Foreign Application Priority Data

Jul. 22, 2010   (JP) ................................. 2010-164616

(51) Int. Cl.
*G06K 9/00*   (2006.01)
*G06K 9/32*   (2006.01)
(Continued)

(52) U.S. Cl.
CPC ............ *G06K 9/3233* (2013.01); *A61B 5/0095* (2013.01); *A61B 8/15* (2013.01); *G10K 15/046* (2013.01); *A61B 2562/0204* (2013.01); *A61B 2562/046* (2013.01)

(58) Field of Classification Search
None
See application file for complete search history.

(56) References Cited

U.S. PATENT DOCUMENTS

| 4,219,846 A | 8/1980 | Auphan ........................ 348/163 |
| 4,307,613 A | 12/1981 | Fox ................................. 73/626 |

(Continued)

FOREIGN PATENT DOCUMENTS

| JP | S54-062684 | 5/1979 |
| JP | 2005-021380 | 1/2005 |

(Continued)

OTHER PUBLICATIONS

M. Xu et al., "Universal Back-Projection Algorithm for Photoacoustic Computed Tomography", *Physical Review E* 71, 016706 (Jan. 19, 2005).

(Continued)

*Primary Examiner* — Chan Park
*Assistant Examiner* — Mai Tran
(74) *Attorney, Agent, or Firm* — Fitzpatrick, Cella, Harper & Scinto (57) ABSTRACT

An image information acquiring apparatus of the present invention includes an acoustic wave detector having, disposed on a reception surface thereof, a plurality of elements that detect acoustic waves generated by an object corresponding to a reconstruction area; an acoustic signal generator that generates acoustic signals that are used in image reconstruction, from the detected acoustic waves; an element selector that selects elements that are used in image reconstruction; and a reconstructor that performs image reconstruction of a point of interest using acoustic signals based on the acoustic waves detected by the selected elements, the image information acquiring apparatus being configured such that, for each selected element, there exists another selected element located at a symmetrical position with respect to a point at which the reception surface is intersected by a perpendicular line drawn from the point of interest to the reception surface.

8 Claims, 7 Drawing Sheets

(51) Int. Cl.
*A61B 5/00* (2006.01)
*A61B 8/15* (2006.01)
*G10K 15/04* (2006.01)

(56) References Cited

U.S. PATENT DOCUMENTS

| | | | |
|---|---|---|---|
| 4,936,308 A * | 6/1990 | Fukukita et al. | 600/438 |
| 5,027,820 A * | 7/1991 | Pesque | 600/443 |
| 5,269,309 A | 12/1993 | Fort et al. | 600/447 |
| 5,465,722 A * | 11/1995 | Fort et al. | 600/447 |
| 5,713,356 A * | 2/1998 | Kruger | 600/407 |
| 5,840,023 A | 11/1998 | Oraevsky et al. | 600/407 |
| 6,623,432 B2 * | 9/2003 | Powers et al. | 600/447 |
| 6,866,632 B1 * | 3/2005 | Chou et al. | 600/443 |
| 6,979,292 B2 | 12/2005 | Kanayama et al. | 600/437 |
| 2005/0004458 A1 | 1/2005 | Kanayama et al. | 600/437 |
| 2005/0054906 A1 | 3/2005 | Page et al. | 600/310 |
| 2005/0187471 A1 | 8/2005 | Kanayama et al. | 600/437 |
| 2005/0203402 A1 | 9/2005 | Angelsen et al. | 600/447 |
| 2007/0060817 A1 | 3/2007 | Davies | 600/437 |
| 2008/0287799 A1 | 11/2008 | Hall et al. | 600/454 |
| 2009/0024038 A1 * | 1/2009 | Arnold | 600/459 |
| 2009/0154244 A1 | 6/2009 | Shiga | 365/185.02 |
| 2010/0011041 A1 * | 1/2010 | Vannucci | 708/400 |
| 2010/0058870 A1 | 3/2010 | Kobayashi | 73/596 |
| 2011/0066023 A1 | 3/2011 | Kanayama et al. | 600/407 |
| 2011/0098550 A1 | 4/2011 | Yoda | 600/407 |
| 2011/0128816 A1 | 6/2011 | Baba et al. | 367/11 |
| 2012/0302864 A1 | 11/2012 | Yoda | 600/407 |
| 2012/0309116 A1 * | 12/2012 | Colgan et al. | 438/5 |

FOREIGN PATENT DOCUMENTS

| | | | |
|---|---|---|---|
| JP | 2005-218684 | 8/2005 | |
| JP | 2010-022812 | 2/2010 | |
| JP | 2010-057730 | 3/2010 | |
| WO | WO 2009/154244 | 12/2009 | |
| WO | WO 2009154244 A1 * | 12/2009 | A61B 8/08 |

OTHER PUBLICATIONS

Office Action issued Apr. 4, 2014 in counterpart Chinese patent application 201180035775.7, with translation.

M. Xu et al., "Photoacoustic Imaging in Biomedicine", *Review of Scientific Instruments* 77, 041101 (Apr. 17, 2006).

Office Action (Notice of Reason for Rejection) issued Sep. 9, 2014, in counterpart Japanese patent application 2010-164616, with translation.

* cited by examiner

IMAGE INFORMATION ACQUIRING APPARATUS, IMAGE INFORMATION ACQUIRING METHOD AND IMAGE INFORMATION ACQUIRING PROGRAM

TECHNICAL FIELD

The present invention relates to an image information acquiring apparatus, an image information acquiring method and an image information acquiring program.

BACKGROUND ART

Ongoing active research is being carried out, in medical fields, on optical imaging devices for obtaining information of the interior of objects such as living bodies using light irradiated from a light source, for instance a laser. Photoacoustic Tomography (PAT) is one such optical imaging technique. Photoacoustic tomography is a technique wherein information associated with values of optical characteristics in the interior of the object can be visualized on the basis of acoustic waves generated by biological tissue, on account of the photoacoustic effect, upon absorption of energy from light that propagates or diffuses through the interior of the object. The information associated with the optical characteristic values is obtained by detecting acoustic waves at a plurality of sites that surround the object, and by subjecting the obtained signals to a mathematical analysis process.

Information obtained thanks to the above technique, in the form of, for instance, a distribution of initial sound pressure or a distribution of light absorption density, as generated through irradiation of light, can be used for, for instance, pinpointing malignant tumor sites associated with the growth of new blood vessels. The photoacoustic effect denotes herein the phenomenon whereby pulsed light that is irradiated onto an object gives rise to ultrasounds (compression waves) as a result of the volume expansion of regions having a high absorption coefficient within the object to be measured. Hereafter, acoustic wave generated as a result of the volume expansion elicited by irradiation of pulsed light will also be referred to as "photoacoustic wave".

In photoacoustic tomography of an object, there is ordinarily measured the change over time of acoustic waves at various points on a closed spatial surface, in particular a spherical measurement surface that surrounds a whole object. If measurements could be carried out using an ideal acoustic detector (wideband/point detection), it would theoretically be possible to visualize completely the initial sound pressure distribution generated as a result of light irradiation. Even in the case of a non-closed space, it is mathematically known that an initial sound pressure distribution generated as a result of light irradiation can be substantially reproduced if the object can be measured in a cylindrical or planar fashion (Non Patent Literature 1).

The following equation (1), called the "photoacoustic wave equation", is a partial differential equation that constitutes the foundation of PAT. Solving the equation allows describing the acoustic wave propagation on the basis of the initial sound pressure distribution, whereby it becomes possible to determine theoretically how and where the acoustic waves can be detected:

[Math. 1]

$$\left(\nabla^2 - \frac{1}{c^2}\frac{\partial^2}{\partial t^2}\right)p(r,t) = -p_0(r)\frac{\partial \delta(t)}{\partial t} \quad (1)$$

where r denotes position,
t denotes time,
p(r, t) denotes the temporal change of sound pressure,
$p_0(r)$ denotes the initial sound pressure distribution,
c is the speed of sound,
$\delta(t)$ is a delta function representing the shape of a light pulse.

Mathematically, image reconstruction in PAT is a so-called inverse problem that involves deriving image data such as initial sound pressure distribution $p_0(r)$ on the basis of the sound pressure $p_d(r_d,t)$ obtained at a detection point. The explanation below refers to a universal back projection (UBP) method that is typically used as an image reconstruction technique in PAT. The inverse problem of determining $p_0(r)$ can be solved accurately by analyzing the photoacoustic wave equation (1) in the frequency space. The UBP represents the result in the time space. Equation (2) below is ultimately derived:

[Math. 2]

$$p_0(r) = -\frac{2}{\Omega_0}\nabla \cdot \int_{S_0} \tilde{n}_0^S dS_0 \left[\frac{p_0(r_0,t)}{t}\right]_{t=|r-r_0|} \quad (2)$$

where $\Omega_0$ denotes the solid angle of an entire measuring area $S_0$ with respect to an arbitrary reconstruction voxel (or point of interest).

Transforming the above equation to an easier to understand form yields Equation (3) below.

[Math. 3]

$$p_0(r) = \int_{\Omega_0} b(r_0, t=|r-r_0|)\frac{d\Omega_0}{\Omega_0} \quad (3)$$

where $b(r_0, t)$ denotes projection data,
$d\Omega_0$ is the solid angle of a detector $dS_0$ with respect to an arbitrary observation point P.

The initial sound pressure distribution $p_0(r)$ can be obtained by performing back projection of the projection data according to the integration of Equation (3).

In Equation (3), the projection data and the solid angle are given by Equation (4) and Equation (5) below.

[Math. 4]

$$b(r_0, t) = 2p(r_0, t) - 2t\frac{\partial p(r_0,t)}{\partial t} \quad (4)$$

$$d\Omega_0 = \frac{dS_0}{|r-r_0|^2}\cos\theta \quad (5)$$

where θ is the angle formed by the detector and the arbitrary observation point P.

In a case where the distance between an acoustic source and a measurement position is large enough in comparison with the size of the acoustic source (acoustic far-field approximation), Expression (6) below applies to $p(r_0, t)$ and Equation (7) below applies to $b(r_0, t)$.

[Math. 5]

$$p(r_0, t) \ll t \frac{\partial p(r_0, t)}{\partial t} \quad (6)$$

$$b(r_0, t) = -2t \frac{\partial p(r_0, t)}{\partial t} \quad (7)$$

In PAT image reconstruction it is known that the initial sound pressure distribution $p_0(r)$ can be determined by obtaining projection data $b(r_0, t)$ through time differentiation of the detection signal $p(r_0, t)$ acquired by the detector, and by performing back projection of the projection data thus obtained according to Equation (3) (Non Patent Literature 1, Non Patent Literature 2).

However, Equation (1), which is the photoacoustic wave equation used for determining Equation (3), assumes, for instance, a constant speed of sound, measurements from all directions, impulse photoexcitation, wideband detection of acoustic waves, point detection of acoustic waves, and continuous acoustic wave sampling. It is not easy to realize in practice a device that satisfies these assumptions.

In an actual object, for instance, it is difficult to obtain acoustic wave detection information over the entirety of a closed space surface that surrounds the whole object. Also, increasing the size of the acoustic wave measurement region requires increasing the size and the number of elements of the acoustic detector, and increasing the signal processing and control burden of each element, all of which translates into greater manufacturing costs. Such being the case, actual measurement devices that utilize PAT techniques are often configured as devices that detect acoustic waves using an acoustic wave detector of restricted size and from a specific direction of the object.

Photoacoustic tomography based on flat plate-type measurement has been proposed as an example of such a device, as disclosed in Patent Literature 1. In this photoacoustic tomography, light is irradiated onto an object sandwiched between flat plates, and acoustic waves are detected by an acoustic wave detector disposed on the flat plate. Herein, light irradiation and acoustic wave reception may take place over a plurality of times. Through light irradiation and acoustic wave reception that are performed over a plurality of times, there may be calculated, and used, a value that results from averaging acoustic signals or averaging respective values that are calculated on the basis of the acoustic signals.

Such a device has various advantages. Specifically, it becomes possible to detect low-noise acoustic waves by detecting acoustic waves such that the object and the acoustic wave detector are closely pressed against a flat plate, the position of the object and the acoustic wave detector can be fixed during repeated detection, and the motion of the acoustic wave detector can be controlled easily.

CITATION LIST

Patent Literature

[PTL 1]
U.S. Pat. No. 5,840,023

Non Patent Literature

[NPL 1]
PHYSICAL REVIEW E 71, 016706 (2005)
[NPL 2]
REVIEW OF SCIENTIFIC INSTRUMENTS, 77, 041101 (2006)

SUMMARY OF INVENTION

Technical Problem

However, the bearing of the acoustic wave detector with respect to object is limited in case of detection of acoustic waves using an acoustic wave detector that is disposed on a flat plate, as in conventional technologies. Signals based on acoustic waves detected by elements on a reception plane of such an acoustic wave detector are used herein for image reconstruction.

In a case where one point on the space in which image reconstruction of the interior of the object is carried out is an acoustic source of photoacoustic waves, then the relationship between that acoustic source and the position of an element group on the reception surface of the acoustic wave detector that detects the acoustic waves is a limited relationship. Upon acoustic wave detection, as a result, the position of the acoustic source is limited such that there is an alignment of acoustic waves that are simultaneously received at elements symmetrically positioned with respect to the acoustic source. An image reconstruction process that uses acoustic signals received simultaneously at elements in symmetrical positions with respect to the acoustic source can be used only for reconstruction relating to an acoustic source of photoacoustic waves that is present directly above the vicinity of the center of the reception surface of the acoustic wave detector (i.e. on the normal line that traverses the center of the reception surface).

As the acoustic source gets nearer the vicinity of the center of the reception surface of the acoustic wave detector, however, the image reconstruction process utilizes acoustic signal groups that are received by elements at non-symmetrical positions, whereupon there increase the discrepancies vis-à-vis the assumptions in the photoacoustic wave equations. As a result, artifacts (images that appear despite the absence of a an acoustic source) occur in the reconstructed image in a case where, in PAT image reconstruction that relies on conventional technologies, the acoustic source of photoacoustic waves is located above (on the normal line of) a position offset from the vicinity of the center of the reception surface of the acoustic wave detector. Even larger artifacts appear in reconstructed images of acoustic sources of photoacoustic waves that are located above the vicinity of the outer edge, or beyond, of the reception surface of the acoustic wave detector.

Even in a case where the acoustic wave detector moves and the signals for each position of the elements of the acoustic wave detector after the movement are averaged, such that the signals are treated as an apparent acoustic signal of a large acoustic wave detector, artifacts occur as well in the same way as when using acoustic signals of elements at non-symmetrical positions. Large artifacts occur likewise at the outer edge portion of the reception surface in a case where signals of the moving acoustic wave detector are treated as signals of a large acoustic wave detector.

In the light of the above problems, it is an object of the present invention to provide a technology for obtaining reconstructed image data having fewer artifacts, upon detection of acoustic waves using an acoustic wave detector that is disposed on a flat plate.

Solution to Problem

This invention provides an image information acquiring apparatus, comprising:
an acoustic wave detector having, disposed on a reception surface thereof, a plurality of elements that detect acoustic waves generated by an object corresponding to a reconstruction area at which image reconstruction is performed;

an acoustic signal generator that generates an acoustic signal that is used in image reconstruction, from the acoustic waves detected by the acoustic wave detector;

an element selector that selects elements that are used in image reconstruction from among the plurality of elements; and a reconstructor that performs image reconstruction of a point of interest within the reconstruction area using acoustic signals based on the acoustic waves detected by the elements selected by the element selector, wherein the element selector selects elements in such a manner that, for each selected element, there exists another selected element located at a symmetrical position with respect to a point at which the reception surface is intersected by a perpendicular line drawn from the point of interest to the reception surface.

This invention also provides an image information acquiring method, comprising the steps of:

detecting acoustic waves generated by an object corresponding to a reconstruction area at which image reconstruction is performed, by way of an acoustic wave detector in which a plurality of elements are disposed on a reception surface;

generating an acoustic signal that is used in image reconstruction, from the acoustic waves detected by the acoustic wave detector;

selecting elements that are used in image reconstruction from among the plurality of elements; and performing image reconstruction of a point of interest within the reconstruction area using acoustic signals based on the acoustic waves detected by the elements selected in the selection step, wherein in the selection step, elements are selected in such a manner that, for each selected element, there exists another selected element located at a symmetrical position with respect to a point at which the reception surface is intersected by a perpendicular line drawn from the point of interest to the reception surface.

This invention also provides an image information acquiring program for causing an information processing device to execute an image information acquiring method that includes the steps of:

detecting acoustic waves generated by an object corresponding to a reconstruction area at which image reconstruction is performed, by way of an acoustic wave detector in which a plurality of elements are disposed on a reception surface;

generating an acoustic signal that is used in image reconstruction, from the acoustic waves detected by the acoustic wave detector;

selecting elements that are used in image reconstruction from among the plurality of elements; and performing image reconstruction of a point of interest within the reconstruction area using acoustic signals based on the acoustic waves detected by the elements selected in the selection step, wherein in the selection step, elements are selected in such a manner that, for each selected element, there exists another selected element located at a symmetrical position with respect to a point at which the reception surface is intersected by a perpendicular line drawn from the point of interest to the reception surface.

Advantageous Effects of Invention

The present invention allows obtaining reconstructed image data having fewer artifacts, upon detection of acoustic waves using an acoustic wave detector that is disposed on a flat plate.

Further features of the present invention will become apparent from the following description of exemplary embodiments with reference to the attached drawings.

DESCRIPTION OF EMBODIMENTS

Preferred embodiments of the image information acquiring apparatus and method according to the present invention will be explained with reference to accompanying drawings. However, the scope of the invention is not limited to the examples in the drawings.

Example 1

The image information acquiring apparatus of the present embodiment is a photoacoustic diagnostic apparatus that detects acoustic waves generated through irradiation of light, and that generates three-dimensional reconstructed image data on the basis of information relating to the detected acoustic waves.

(Device Configuration)

Figure 1:
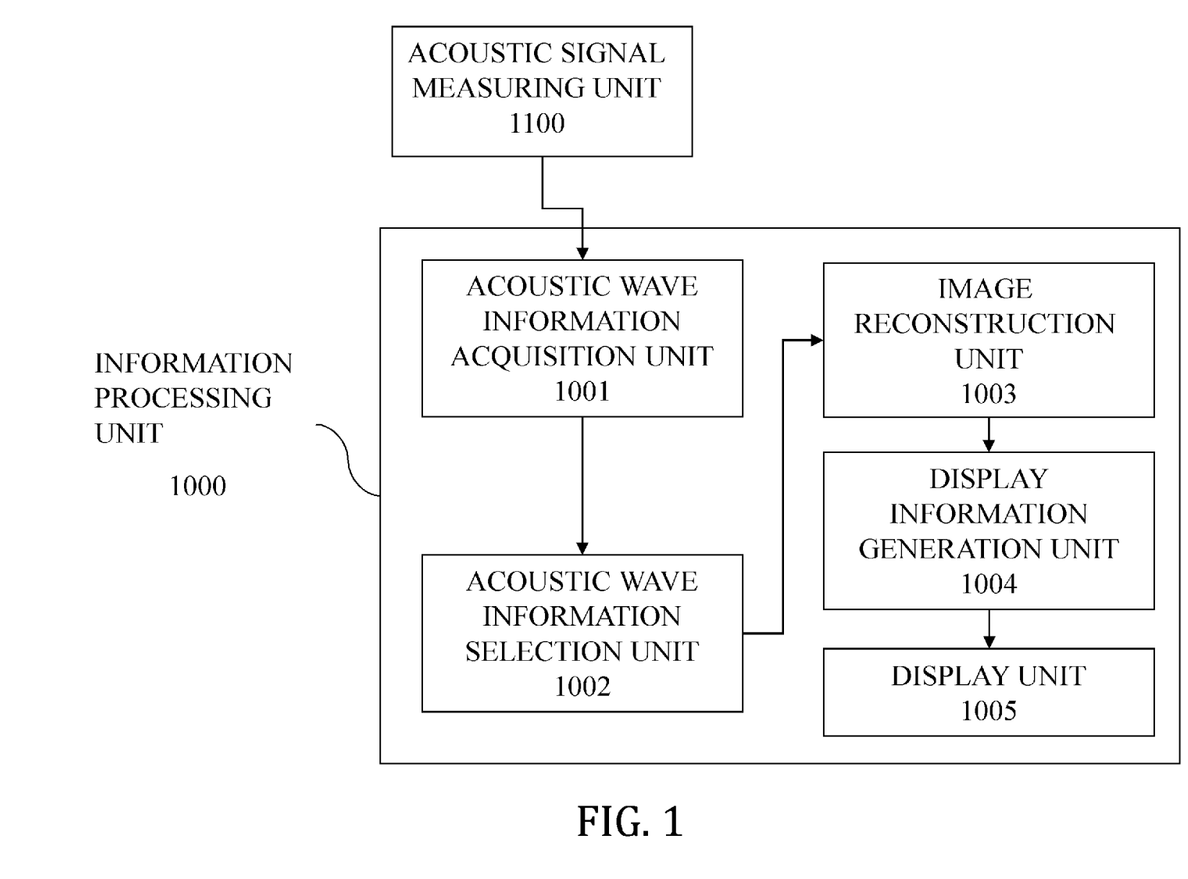
FIG. 1 is a block diagram illustrating the configuration of an image information acquiring apparatus of Example 1.
Figure 3:
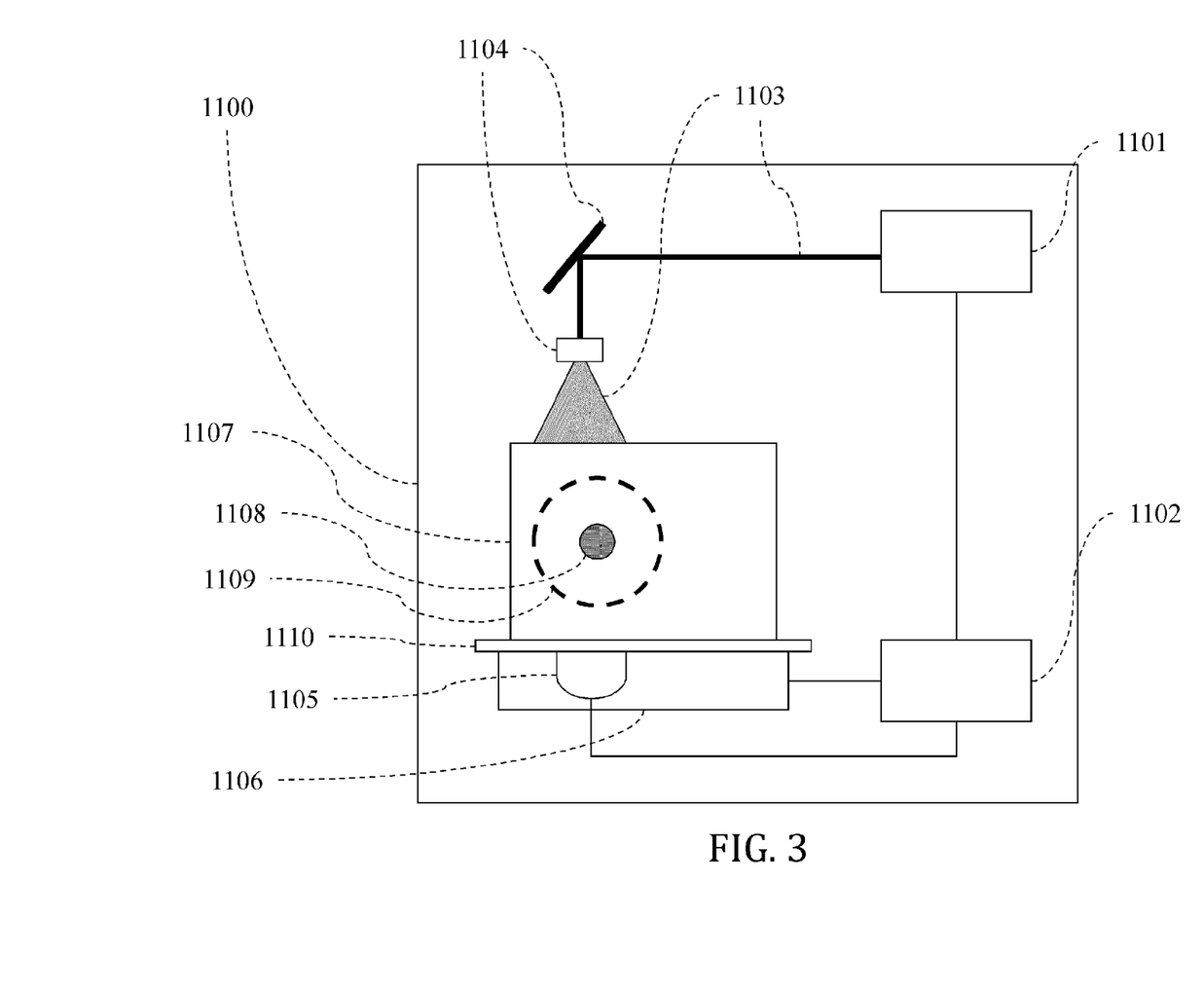
FIG. 3 is a diagram illustrating the configuration of an acoustic signal measuring unit in Example 1.

FIG. 1 is a block diagram illustrating the functional configuration of a photoacoustic diagnostic apparatus according to the present example. As illustrated in FIG. 1, the photoacoustic diagnostic apparatus according to the present example comprises an information processing unit 1000 and an acoustic signal measuring unit 1100. As explained in detail below, the acoustic signal measuring unit 1100 transmits, to the information processing unit 1000, acoustic signal information and information relating to the position of elements on a reception surface of an acoustic wave detector 1105 (FIG. 3). The acoustic wave detector 1105 is, for instance, a probe that detects acoustic waves, for instance ultrasound waves. Herein, information relating to an element position may be position information of an element on the reception surface of the acoustic wave detector 1105, or may be an identifier of an element for mapping to some other position information.

In the disclosure below, the term "acoustic signal" denotes signals such that photoacoustic waves generated by an object, and received by an acoustic wave detector, are converted to electric signals that can be used for image reconstruction (image data generation) through amplification and digital conversion by the control unit 1102. The acoustic signal measuring unit 1100 may transmit information that identifies an element of the acoustic wave detector, as well as acoustic signal information in the form of the acoustic signal itself, or may transmit acoustic signal information in the form of information resulting from performing correction, such as element sensitivity correction, gain correction and the like. In the case of a photoacoustic diagnostic apparatus, in particular, there may be carried out photoacoustic signal acquisition and light irradiation over a plurality of times, such that there is transmitted averaged information, for acoustic signal information obtained through reception, by an acoustic wave detector, of photoacoustic waves generated through irradiation of light onto an object. The control unit corresponds to the acoustic signal generator of the present invention.

The information processing unit 1000 performs a three-dimensional image reconstruction process by selecting acoustic signal information of elements that are deemed to be at symmetrical positions, for each position within a reconstruction area, on the basis of acoustic signal information and information relating to the position of the elements as obtained by the acoustic signal measuring unit 1100. The information processing unit 1000 generates display image data on the basis of the generated three-dimensional reconstructed image data, and displays the display image data.

The information processing unit 1000 comprises an acoustic wave information acquisition unit 1001, an acoustic wave information selection unit 1002, an image reconstruction unit 1003, a display information generation unit 1004 and a display unit 1005. The acoustic wave information acquisition unit 1001 acquires acoustic signal information transmitted by the acoustic signal measuring unit 1100, and sends the information to the acoustic wave information selection unit 1002. The acoustic wave information selection unit 1002 selects acoustic signal information used for image reconstruction, for each point of an area at which image reconstruction is carried out, and sends the information to the image reconstruction unit 1003.

The image reconstruction unit 1003 performs three-dimensional image reconstruction using only the selected acoustic signal information, for each point within the area at which image reconstruction is to be carried out, and generates three-dimensional image data (volume data) on the basis of the acoustic signal information. In the case of a photoacoustic diagnostic apparatus, in particular, modifying the wavelength of irradiated light allows generating three-dimensional image data that is reconstructed on the basis of values resulting from calculating an absorption coefficient distribution, relating to each wavelength, of the interior of the object. The generated three-dimensional reconstructed image data is sent to the display information generation unit 1004. The information transmitted by the acoustic signal measuring unit 1100 and used in the reconstruction process may include, for instance, information relating to volume data, the size of the acoustic wave detector, and element pitch and directionality. There may also be used information stored beforehand in a storage medium or the like.

In the present example as explained herein, the acoustic signal information is sent, once selection is over, to the image reconstruction unit 1003, whereupon there starts the image reconstruction process. However, a configuration is also possible wherein the acoustic wave information selection unit 1002 sends, to the image reconstruction unit 1003, acoustic signal information already selected for each point within the area at which image reconstruction is to be carried out, and there is selected acoustic signal information of a next point while image reconstruction process is being executed in parallel.

The display information generation unit 1004 generates information to be displayed on the display unit 1005, on the basis of the generated three-dimensional reconstructed image data. The display information may be any display information, so long as it is generated on the basis of three-dimensional image information (three-dimensional reconstructed image data). For instance, the image information may be two-dimensional image data obtained by volume rendering, multiplanar reformation display, maximum intensity projection or the like. Other display information, for instance statistical information, may also be generated on the basis of information obtained from the three-dimensional image information. Using irradiation light of dissimilar wavelengths in the photoacoustic diagnostic apparatus allows obtaining three-dimensional image information based on values of an absorption coefficient distribution within the object in accordance with the wavelength. Comparing these values with the wavelength dependence that is specific to the substances that make up biological tissue allows imaging the concentration distribution of substances that make up a living body, and allows displaying statistical information of each value in the form of numerical values, graphs, histograms or the like. Examples of substances that make up biological tissue include, for instance, glucose, collagen, oxy/deoxy hemoglobin and the like.

The display unit 1005 is a display device, such as a graphic card, a liquid crystal or a CRT display, for displaying the display information generated by the display information generation unit 1004.

Figure 2:
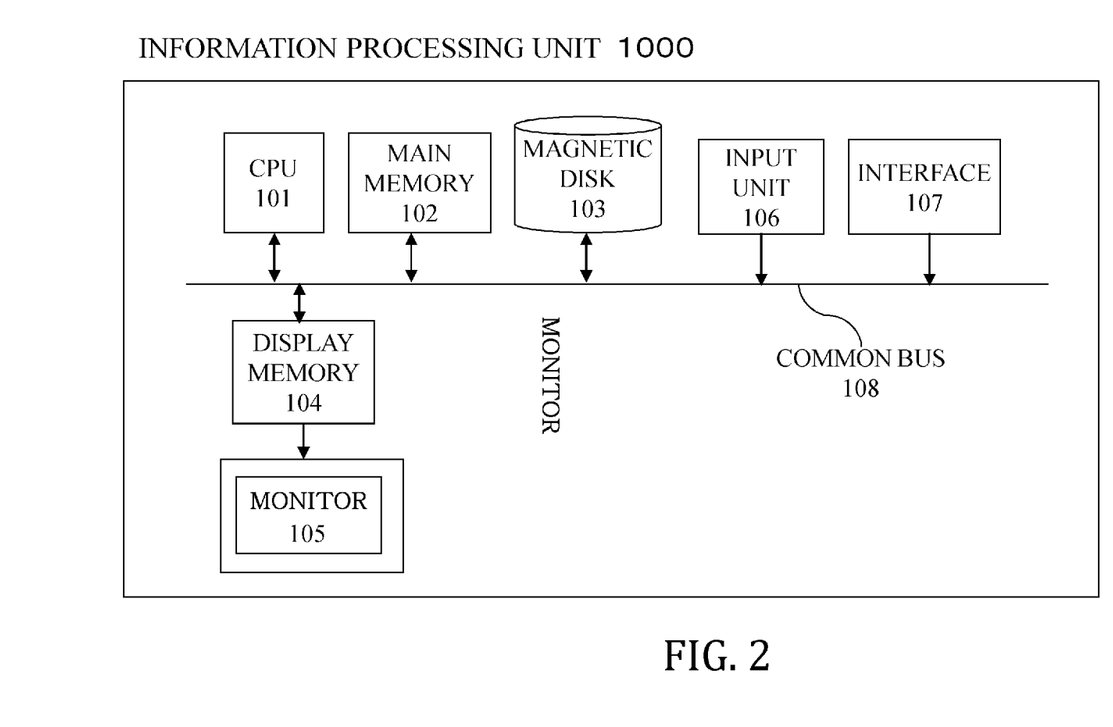
FIG. 2 is a diagram illustrating a configuration wherein the information processing unit of Example 1 is realized in the form of software.

The process performed by the information processing unit 1000 may be carried out in the form of hardware using circuits and devices corresponding to the various units, or may be carried out in the form of software that is run in a computer or the like. FIG. 2 is an example illustrating the basic configuration of a computer for executing, in the form of software, the functions of the units in the information processing unit 1000.

Broadly, a CPU 101 controls the operation of each constituent element of the information processing unit 1000. A main memory 102 stores a control program executed by the CPU 101, and provides a work area during execution of the program by the CPU 101. A magnetic disk 103 stores, for instance, an operating system (OS), device drivers for peripherals, and various application software items including a program for executing, among others, the processes in the below-described flowcharts. A display memory 104 stores temporarily display data for a monitor 105. The monitor 105 is, for instance, a CRT display or a liquid crystal monitor that displays images on the basis of data from the display memory 104.

An input unit 106 performs, for instance, pointing input and character input prompted by an operator, for instance through a mouse, keyboard or the like. In an example of the present invention, operations by the operator are performed via the input unit 106. An interface 107 is an interface for performing exchange of various data between the information processing unit 1000 and the exterior, and may be configured according to IEEE1394, USB, Ethernet Port™ or the like. Data acquired via the interface 107 is stored in the main memory 102. The function of the acoustic signal measuring unit 1100 is realized via the interface 107. The above-described constituent elements are connected, so as to be capable of communicating with each other, via a common bus 108.

FIG. 3 is a diagram illustrating an example of a configuration in a case where the acoustic signal measuring unit 1100 is a photoacoustic diagnostic apparatus. A light source 1101 is a light source of irradiation light that is irradiated onto an object, for instance a laser or a light-emitting diode. The irradiation light is light of a specific wavelength that is absorbed by specific components from among the components that make up the object.

The control unit 1102 controls the light source 1101, an optical device 1104, the acoustic wave detector 1105 and a position controller 1106. The control unit 1102 amplifies the electric signals of the photoacoustic waves obtained by the acoustic wave detector 1105, and converts analog signals to digital signals. The control unit 1102 performs various types of signal processing and correction processing, as the case may require. Also, the acoustic signal information is transmitted from the acoustic signal measuring unit 1100 to an external device, such as the information processing unit 1000, via an interface not shown.

From among the processes carried out by the control unit 1102, an example of the control of the light source and the optical device may involve control of the timing, waveform, intensity and so forth of the laser irradiation. The position controller 1106 of the acoustic wave detector performs control so as to bring the position of the acoustic wave detector 1105 to an appropriate position. The control unit 1102 performs also control for measuring the acoustic signal detected by the acoustic wave detector 1105 in synchrony with the timing of laser irradiation. The control unit 1102 further performs signal processing, for instance calculation of an average value of acoustic signals for each element through additive averaging of acoustic signals for each element as obtained through irradiation with laser over a plurality of times.

The optical device 1104 is, for instance, a mirror that reflects light or a shape-changing lens that condenses or magnifies light. Any such optical components may be used, provided that light 1103 emitted by the light source can be irradiated, in a desired shape, onto an object 1107. The light 1103 irradiated by the light source 1101 can be transmitted by way of, for instance, an optical waveguide or the like. The optical waveguide is preferably an optical fiber. In a case where an optical fiber is used, light can be led to a living body surface by using a plurality of optical fibers for respective light sources. Alternatively, light from a plurality of light sources may be guided along one single optical fiber, such that all the light is guided to the light source using one optical fiber alone. The light source 1101 and the optical device 1104 may each be provided as a plurality thereof.

Through control by the control unit 1102 configured as described above, the light 1103 generated by the light source 1101 is irradiated to the object 1107 via the optical device 1104, whereupon a light-absorbing body (acoustic source) 1108 inside the object absorbs the light and generates a photoacoustic wave 1109.

The acoustic wave detector 1105 comprises, for instance, a transducer that relies on piezoelectric phenomena, a transducer that relies on optical resonance, or a transducer that relies on capacitance changes. Any such acoustic wave detector may be used, so long as the detector can detect acoustic waves. The acoustic wave detector 1105 may detect acoustic waves by coming directly into contact with the object 1107. Alternatively, the object may be pressed using a plate such as a flat plate 1110, and may detect the photoacoustic wave 1109 of the pressed object that gets across the flat plate.

The explanation of the acoustic wave detector of the present example assumes that a plurality of elements (detection elements) are arranged two-dimensionally. Using such two-dimensionally arrayed elements allows detecting acoustic waves at a plurality of sites simultaneously, allows shortening the detection time, and allows reducing the influence of, for instance, vibration in the object. Also, it is desirable to use an acoustic impedance matching agent, not shown, such as a gel, water or the like, which is arranged between the acoustic wave detector 1105 and the object, for suppressing the reflection of acoustic waves.

The acoustic wave detector 1105 or the region at which light is irradiated onto the object may be movable. The optical device 1104 can be configured in such a manner that the light generated by the light source can move over the object. Methods for moving the region at which light is irradiated on the object include, for instance, methods that utilize movable mirrors or the like, or methods in which the light source itself is moved by mechanical means. Also, the acoustic wave detector 1105 may be caused to move by the position controller 1106 that shifts the position of the acoustic wave detector 1105. In an example of the position controller 1106, the acoustic wave detector 1105 may be caused to move over the flat plate 1110 by a motor, on the basis of information from a position sensor.

The control unit 1102 controls the position of the region at which light is irradiated and the position of the acoustic wave detector 1105. The control unit 1102 can perform control in such a manner that the region at which light is irradiated onto the object 1107 (light irradiated onto the object) and the acoustic wave detector 1105 are moved in synchrony. Light can be irradiated over a wider area if the light irradiation region is movable. Also, moving the acoustic wave detector allows detecting photoacoustic waves at an appropriate position with respect to the irradiation region.

(Operational Procedure)

Figure 4:
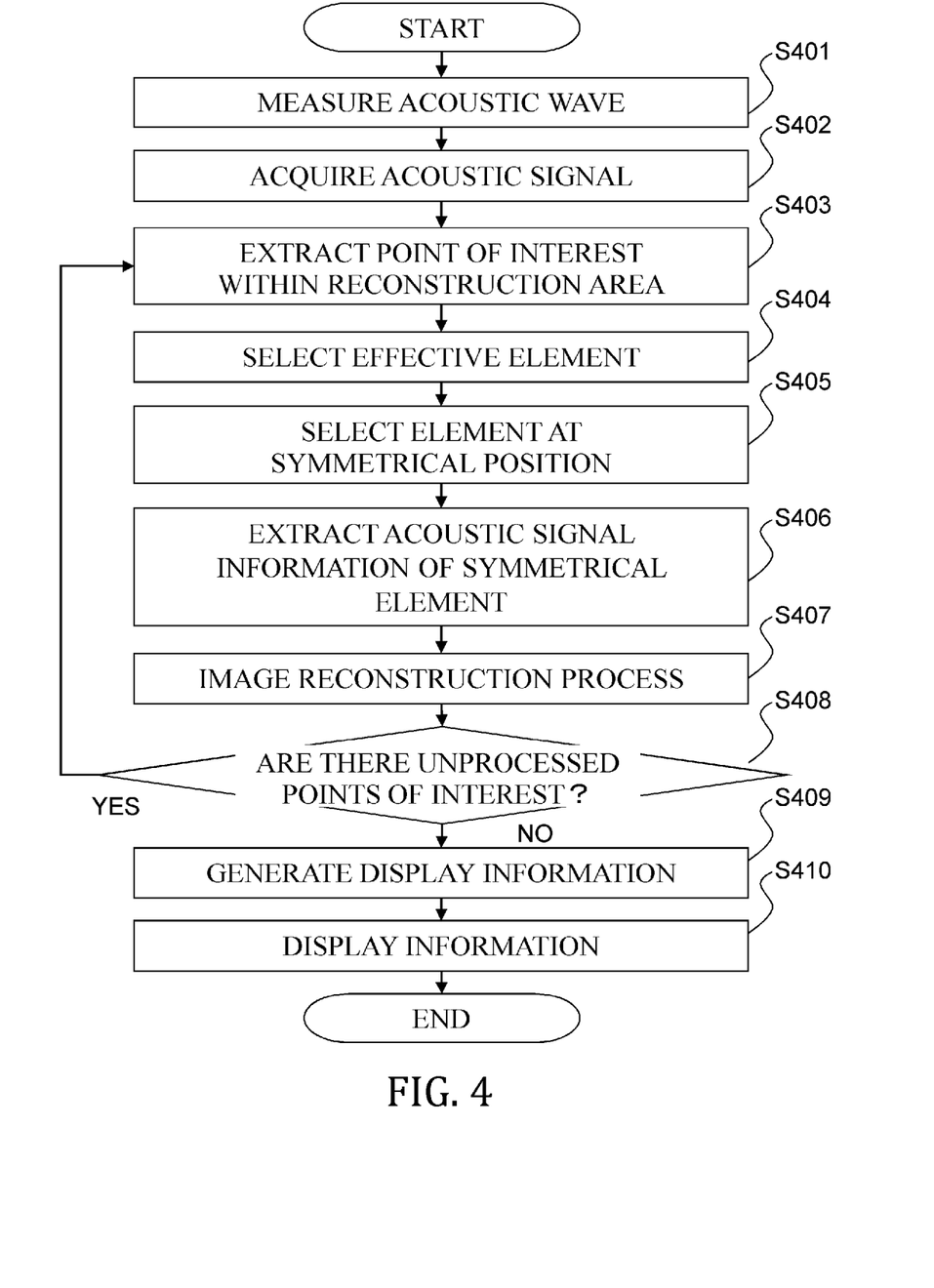
FIG. 4 is a flowchart illustrated in a process procedure in Example 1.
Figure 5:
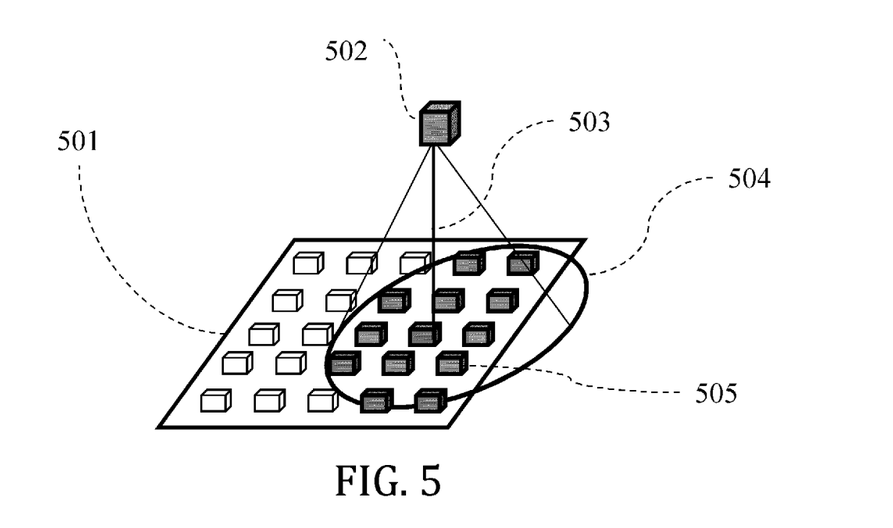
FIG. 5 is a diagram illustrating a selection range of effective elements in Example 1.
Figure 6:
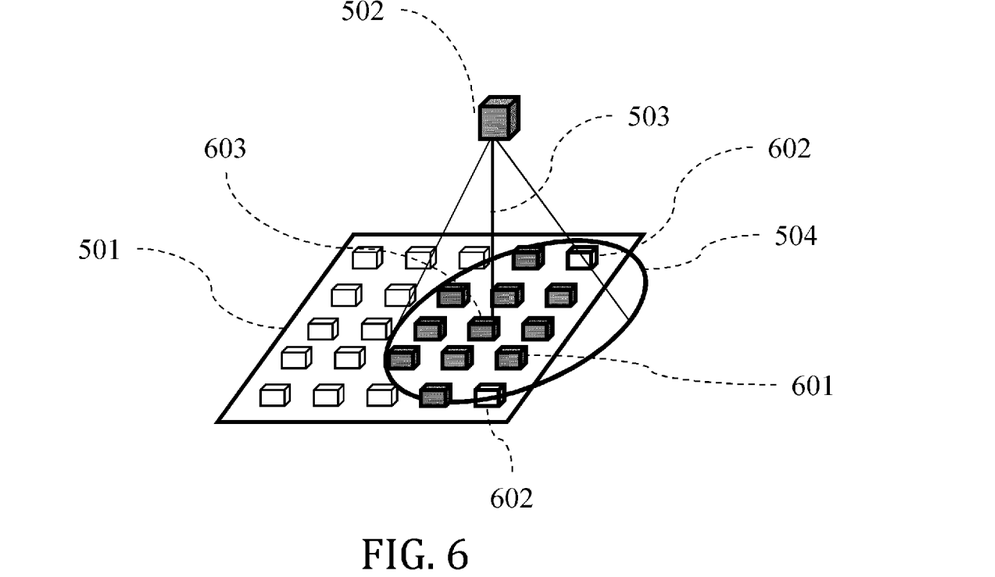
FIG. 6 is a diagram illustrating elements at symmetrical positions in Example 1.

An explanation follows next, with reference to the flowchart of FIG. 4 and FIGS. 5 and 6, on the procedure of a specific process executed by the photoacoustic diagnostic apparatus of the present example.

A procedure for carrying out image reconstruction through selection of acoustic signal information will be explained next with reference to the flowchart of FIG. 4. The start of the flowchart of FIG. 4 corresponds to a state in which the photoacoustic diagnostic apparatus has been started up and the acoustic signal measuring unit 1100 has begun measuring an object.

In step S401, the acoustic signal measuring unit 1100 starts a measurement process, irradiates laser light a plurality of times onto the object, and receives photoacoustic waves, generated by the object, at the acoustic wave detector. The control unit 1102 analyzes a photoacoustic signal from the received photoacoustic wave in synchrony with the irradiation of laser light, and calculates a value that is an additive average over the number of laser irradiations, for each element.

In step S402, the acoustic wave information acquisition unit 1001 acquires acoustic signal information from the acoustic signal measuring unit 1100. If configured as in FIG. 2, the information processing unit 1000 acquires information via the interface 107. The acquired acoustic signal information is stored in, for instance, a storage medium, and is sent to the acoustic wave information selection unit 1002. In a case where the information processing unit 1000 is configured as in FIG. 2, the information is stored in the main memory 102 and the magnetic disk 103.

The method for acquiring the acoustic signal may be a method in which the signal is acquired through transmission of a command from the information processing unit 1000, via the interface 107, or a method in which signals are sequentially sent by the acoustic wave information acquisition unit 1001. In an alternative procedure, the information processing unit 1000 may instruct beforehand the signal measuring unit 1100 to perform an acoustic measurement of an object and acquire acoustic wave information. In this example, the acoustic signal information acquired by the acoustic wave information acquisition unit 1001 is a photoacoustic signal for each additively-averaged element.

The acoustic wave measuring unit 1100 may also acquire, simultaneously, information relating to the acoustic wave detector. Alternatively, there may by the acquired just an ID that identifies the acoustic wave detector, and there may be used information relating to the acoustic wave detector as stored beforehand in the information processing unit 1000 (in the magnetic disk 103 in the configuration of FIG. 2). Information relating to the acoustic wave detector may include, for instance, information relating to the acoustic wave reception performance of the acoustic wave detector, such as size of the acoustic wave detector, element pitch, element count, element layout, element directionality and the like, as well as element position information.

In step S403, the acoustic wave information selection unit 1002 extracts one point at which the image reconstruction process is not yet carried out, as a point of interest in an area to be reconstructed. The area to be reconstructed is an area within the object for which a three-dimensional image reconstruction process is to be carried out, and is a measurement region of the acoustic signal measuring unit 1100. However, the example of the present invention can be used also in an instance where only part of the measurement region of the acoustic signal measuring unit 1100 is the area to be reconstructed.

The point of interest in the area to be reconstructed is one point on a three-dimensional space of the reconstruction area. A point of interest corresponds to each voxel in generated three-dimensional reconstructed image data (volume data) in a case where the image reconstruction process is carried out so as to calculate volume data defined with a desired resolution, in the area to be reconstructed. In the present example, the point of interest in the reconstruction area results from extracting one voxel from among volume data that is generated by image reconstruction.

In step S404, the acoustic wave information selection unit 1002 selects, as an effective element, an element group for which there can be detected a photoacoustic signal of effective level for the point of interest, from the element group of the reception surface of the acoustic wave detector, in the point of interest extracted in step S403.

For instance, the photoacoustic wave generated by the object may propagate through the interior of the object and reach thereafter any element of the reception surface. However, it is impossible to detect photoacoustic signals of effective level at all the elements, on account of the relationship vis-à-vis the directionality of the acoustic wave detector elements. Therefore, in a case where there is an acoustic source of photoacoustic waves at a position of an object corresponding to a point of interest, an element located at a position such that the point of interest is contained within the directionality range of the element can be considered as an element that allows detecting a photoacoustic signal of effective level. Such an element can be regarded as equivalent to an element that is present within a directionality range, being a range of effective elements for the point of interest, upon superposition of the directionality range of the elements perpendicularly to the reception surface of the acoustic wave detector from the point of interest. That is, an element directionality range may be calculated for one point of interest, and an element group present within that range may be selected as an effective element.

FIG. 5 illustrates an example of selection of elements, on the reception surface of the acoustic wave detector, within a directionality range from a point of interest. An acoustic wave detector 501 of FIG. 5 is an example of the acoustic wave detector 1105 according to the present example.

On the reception surface in the acoustic wave detector 501, there are disposed 25 elements that receive acoustic waves. When calculating an area that is contained within the element directionality range from the point of interest (voxel) 502, a circular area having a predetermined radius and centered around the base of a perpendicular line 503 that is drawn to the reception surface of the acoustic wave detector 501 is obtained as an effective element area 504. That is, the effective element area 504 denotes an area in which there are present elements for which the point of interest 502 can lie within a directionality range of the element. The elements disposed on the effective element area 504 are selected as effective elements 505 on the reception surface of the acoustic wave detector 501.

In an acoustic wave detector on which elements of dissimilar sensitivity are disposed, a method for extracting an element group that can detect an effective-level photoacoustic signal may conceivably involve selecting elements according to a detection purpose. An element selection method may concomitantly be used that includes an additional condition whereby there are excluded elements that impair performance on account of some fault.

The present example can be used regardless of the format and saving method of the information on the extracted element group. As an example, an ID that identifies the elements may be temporarily stored, as information for each point of interest, in the main memory 102. As information relating to the acoustic wave detector, such as element directionality or element position for each identifier, there may be used, for instance, information stored beforehand in the main memory 102 or the magnetic disk 103. The information may be acquired from the acoustic wave measuring unit 1100, together with the acoustic signal information.

In step S405, the acoustic wave information selection unit 1002 selects elements at symmetrical positions, from among the effective elements that are extracted in step S404. The acoustic wave information selection unit 1002 corresponds to the element selector of the present invention. Herein, elements at symmetrical positions denote a group of elements that are positioned at an equal-section angle within a circle that is concentric with the base of a perpendicular line drawn from the point of interest to the reception surface, from among the above-described effective element group. Herein, there are two elements at substantially point-symmetrical positions among elements disposed in the form of a square grid on the reception surface of the acoustic wave detector. However, the group of elements at symmetrical positions on the reception surface is not limited to two elements in a case where the elements are located at respective vertices of a regular polygon whose centroid is positioned at the base of a perpendicular line from the point of interest.

The element group is positioned in such a manner that the distances between two points are substantially identical and in such a manner that the slopes of straight lines that join the point of interest with the elements on the reception surface have substantially the same slope with respect to the perpendicular line from the point of interest to the reception surface of the acoustic wave detector. The elements in the element group are positioned, on the reception surface, at equal-section angles within a circle centered on the base of the perpendicular line. Therefore, the element group is a group of elements that allow detecting acoustic signal information that is symmetrical with respect to point of interest upon use of the acoustic signals from the elements on the reception surface.

In a case where an acoustic source of photoacoustic waves is present at the point of interest, the element positioned at the base of the perpendicular line does not yield an acoustic signal whose symmetry is lost. In the present step, therefore, that element can be included among the elements at symmetrical positions.

FIG. 6 illustrates an example of selection of elements at symmetrical positions. The acoustic wave detector 501 of FIG. 6 is an example of the acoustic wave detector 1105 according to the present example. The point of interest (voxel) 502, the perpendicular line 503 and the effective element area 504 are the same as those in FIG. 5, and an explanation thereof will be omitted. An effective element at a symmetrical position with respect to the position of the base of the perpendicular line from the point of interest 502 exists for all elements 601 located at symmetrical positions (indicated by shading), from among the effective elements 505 of FIG. 5. On the other hand, no element at a symmetrical position with respect to the position of the base of the perpendicular line exists, in the effective element area 504, for an element 602 located at a non-symmetrical position.

An element 603 in the vicinity of the base of the perpendicular line is at a position such that the element 603 itself can be taken as an element located at a symmetrical position. In the image reconstruction process of the point of interest 502, acoustic signal information of the element 603 in the vicinity of the base of the perpendicular line is not an instance of acoustic signal information whose symmetry is lost, and hence the element 603 can be selected as a symmetrical-position element.

The reconstruction area may be limited. Specifically, there is no condition-matching point of interest (voxel) that is positioned directly above the outer peripheral portion of the reception surface of the acoustic wave detector. Therefore, the reconstruction area can be limited in such a manner that image reconstruction is performed only for points of interest above an area that lies inwards, by at least one row of elements, from the outer peripheral portion of the reception surface. As a result, there may be generated reconstructed image data only at areas that exhibit few artifacts.

Constraints may be imposed on the selection of elements at symmetrical positions in step S405. For instance, a constraint may be imposed whereby, in addition to the condition that mandates the presence of another element at a symmetrical position with respect to the base of the perpendicular line, the selected element group should also lie within a substantially circular or substantially square area. In other words, the outward elements in an element group may be selected in such a manner that the distances from the elements to the base of the perpendicular line are substantially identical. Alternatively, there may be selected only elements such that the numbers of elements over, under, to the left and to the right of the element match one another. Limiting thus the reconstruction area entails a smaller area, but allows obtaining a three-dimensional reconstructed image having fewer symmetrical artifacts. Information relating to such constraints may be instructed by the user upon each reconstruction. Alternatively, there may be used predetermined values stored beforehand in the device. In a case where the information processing unit has the configuration of FIG. 2, the user issues an instruction via the input unit 106, and a predetermined value is stored in the magnetic disk 103.

In step S406, the acoustic wave information selection unit 1002 extracts, as acoustic signal information that is used for image reconstruction of the point of interest, acoustic signal information detected for symmetrical-position elements as selected in step S405, from among the acoustic signal information acquired in step S402.

In step S407, the image reconstruction unit 1003 performs a three-dimensional image reconstruction process on the basis of the acoustic signal information extracted in step S406. In the present step, the light absorption coefficient at the point of interest (voxel) is calculated and stored in a memory (for instance, main memory 102).

Using acoustic signal information selected according to such a procedure allows reducing the influence exerted on the image reconstruction process by the asymmetry of individual acoustic signal information, which is a cause of artifacts. As a result there can be achieved reconstructed images having few artifacts, even in an image reconstruction process that utilizes reconstruction techniques, such as UBP or the like, similar to conventional techniques.

In step S408 it is determined whether a point of interest (voxel) for which three-dimensional image reconstruction is not yet carried out is present or not in the reconstruction area. If there is an unprocessed point of interest, the process of steps S403 to S408 is repeated until that is no longer the case. The image reconstruction unit 1003 sends the volume data to the display information generation unit 1004 when there are no more unprocessed points of interest and image reconstruction process is over for all the voxels of the volume data that denote the reconstruction area. The transmitted volume data is volume data (three-dimensional reconstructed image data) such that voxel values are stored in the form of values calculated on the basis of the measured acoustic signals. For instance, a light absorption coefficient distribution based on photoacoustic signals is stored as the voxel value.

In step S409, the display information generation unit 1004 generates display information for display of volume data that represents the image-reconstructed light absorption coefficient distribution, and sends the display information to the display unit 1005. Herein, the display information may be any information, so long as the information enables display on the basis of the voxel values and volume data generated through the three-dimensional image reconstruction. For instance, the display information may be information for display of two-dimensional display image data generated from the volume data in accordance with various methods. Examples of such methods include, for instance, MIP (Maximum Intensity Projection), MPR (Multi-Planar Reconstruction), volume rendering, surface rendering and the like. The display information may be in the form of numerical values or generated graphs and histograms using, as statistical information, the light absorption coefficient distribution denoted by the voxel values of the volume data.

In step S410, the display device 1005 displays the display information sent by the display information generation unit 1004.

Executing a procedure such as the above-described one allows generating and displaying volume data, having few artifacts, that denotes the light absorption coefficient distribution that is measured by the photoacoustic diagnostic apparatus.

The elements of the acoustic wave detector 1105 of the present example have been exemplified as being disposed on a plane. However, a process identical to that of the present example can be carried out also in the case of an acoustic wave detector in which elements are disposed on a curved surface, for instance a bowl-shaped surface.

Example 2

In the image information acquiring apparatus according to Example 1 an example of a three-dimensional image reconstruction process has been explained in which the reconstruction area is an area above a reception surface of an acoustic wave detector, and in which there is used acoustic signal information of elements selected from among elements on the reception surface of the acoustic wave detector. In the present example, unlike in Example 1, the acoustic wave detector is moved, and a reception area is a combination of the reception surface at each position. Herein, a three-dimensional image reconstruction process is carried out in which the reconstruction area is an area above the reception area, using acoustic signal information of elements selected from among elements at each position within the reception area.

Specifically, there is generated acoustic signal information and an element on the reception area that are handled as equivalent to acoustic signal information and an element on the reception surface of the acoustic wave detector, and there are selected an element of the present invention in acoustic signal information and an element on a reception area, as well as acoustic signal information. Hereafter, the image information acquiring apparatus according to the present example will be explained focusing on features different from those of Example 1.

(Device Configuration)

The configuration of the image diagnostic device according to the present example is identical to that of Example 1 illustrated in FIG. 1, and hence a detailed explanation thereof will be omitted. The configuration itself of the acoustic signal measuring unit 1100 is identical to that illustrated in FIG. 3, although some of the functions are different from those in Example 1. The acoustic signal information and the element selection range in the acoustic wave information selection unit 1002 of the information processing unit 1000 are also different.

The control unit 1102 of the acoustic signal measuring unit 1100 controls the optical device 1104 to appropriately modify thereby the light irradiation position. At the same time, the control unit 1102 controls the position of the acoustic wave detector 1105, by way of the position controller 1106, to move the area on the object to be measured. The area that combines the reception surface of the acoustic wave detector 1105 constitutes the reception area that can receive an effective acoustic signal. Given that virtual elements are present at each position on the reception area, the acoustic signal information received at elements at each position is handled as acoustic signal information of virtual elements. Unlike in Example 1, now it is information relating to the position of virtual elements on the reception area that is sent to the information processing unit 1000.

A plurality of pieces of acoustic signal information of virtual elements may be obtained in case of overlap of the reception surface of the acoustic wave detector 1105 at respective positions. In such cases, the acoustic signal information at respective overlapping positions may be averaged. The average value of the acoustic signal information is then sent to the information processing unit 1000.

The method for designating the reception area may be any method, so long as the method yields an area that combines the areas occupied by a reception surface during motion of the acoustic wave detector 1105. For instance, the acoustic wave detector 1105 may be moved in such a manner that the reception area is an area necessary for reconstruction of a predetermined reconstruction area. Alternatively, the image reconstruction area may be an area above the reception area defined on the basis of a range of motion of the acoustic wave detector 1105.

In the designation method of the respective areas, there may be used a value designated beforehand by the user via the input unit 106 of the information processing unit 1000. Alternatively, the designation method may be a method that utilizes information stored, for instance, in a storage medium of the information processing unit 1000, or a method such that a specific area within the object, defined in accordance with some other measurement method, is handled as a reconstruction area.

The functions of the various units of the information processing unit 1000 can be realized by way of software run in a computer. The basic configuration of such a computer is identical to that of FIG. 2, and hence a detailed explanation thereof will be omitted.

(Operational Procedure)

The procedure itself of the specific process executed by the image diagnostic device of the present example is identical to the procedure of the process of Example 1 illustrated in FIG. 4. However, the following features are different in the various steps. Specifically, the selected elements are not elements on the reception surface of the acoustic wave detector, but virtual elements disposed on a reception area. The acoustic signal information of each element is the acoustic signal information of each virtual element. The operational procedure will be explained with reference to FIG. 7 and the flowchart of FIG. 4, focusing on the differences between the elements.

In the explanation of the present example, the rectangular motion range of the acoustic wave detector of the acoustic signal measuring unit is moved as a whole, the reception area is a rectangular area that matches the entire motion range of the acoustic wave detector, and the reconstruction area is a parallelepiped over the reception area.

In step S401, the acoustic signal measuring unit 1100 measures acoustic waves. In the present example, in particular, measurement is performed by moving together the light irradiation position and the acoustic wave detector. To measure photoacoustic waves, specifically, the control unit 1102 controls the optical device 1104 so as to appropriately modify the light irradiation position. The position controller 1106 measures photoacoustic waves by controlling the position of the acoustic wave detector so that the acoustic wave detector moves over the flat plate 1110 that is pressed against the object.

Light is irradiated at each position to which the acoustic wave detector moves, such that photoacoustic waves are received at all the elements. The photoacoustic waves are temporarily stored, by the control unit 1102, as acoustic signals of the elements at each position, and are re-allocated for each position of the virtual element of the entire reception area. In a case where a plurality of acoustic signals are present for virtual elements at a same position, the acoustic signal information can be calculated in accordance with a method that involves, for instance, additive averaging.

In case of photoacoustic waves, there are instances where acoustic signals cannot be treated as equivalent, even if the positions of the acoustic wave detector or of the elements on the acoustic wave detector match one another. In some cases, for instance, identical light cannot be irradiated at all times onto the entire reconstruction area of the object. In such instances, photoacoustic waves from the light-absorbing body 1108 at a given position may fail to conform to the same conditions for each acoustic wave measurement. To simplify the explanation of the present example, measurements are performed in a state where sufficient light is irradiated at all times onto areas, in the object, that allow measuring photoacoustic waves according to the position of the acoustic wave detector.

The acoustic signal measuring unit sends, to the information processing unit 1000, information relating to the position of the virtual elements on the reception area and acoustic signal information for each position of the virtual elements.

In step S402, the acoustic wave information acquisition unit 1001 acquires information relating to the position of the virtual elements on the reception area, as well as acoustic signal information for each position of the virtual elements, instead of information relating to acoustic signal information and the position of elements on the reception surface, and sends the information to the acoustic wave information selection unit 1002.

In step S403, the acoustic wave information selection unit 1002 decides a reconstruction area as an area above the reception area. Otherwise, the process is identical to that of Example 1.

In step S404, the acoustic wave information selection unit 1002 selects an effective element from among virtual elements on the reception area, and not from among elements on the reception surface. Otherwise, the process is identical to that of Example 1.

Figure 7:
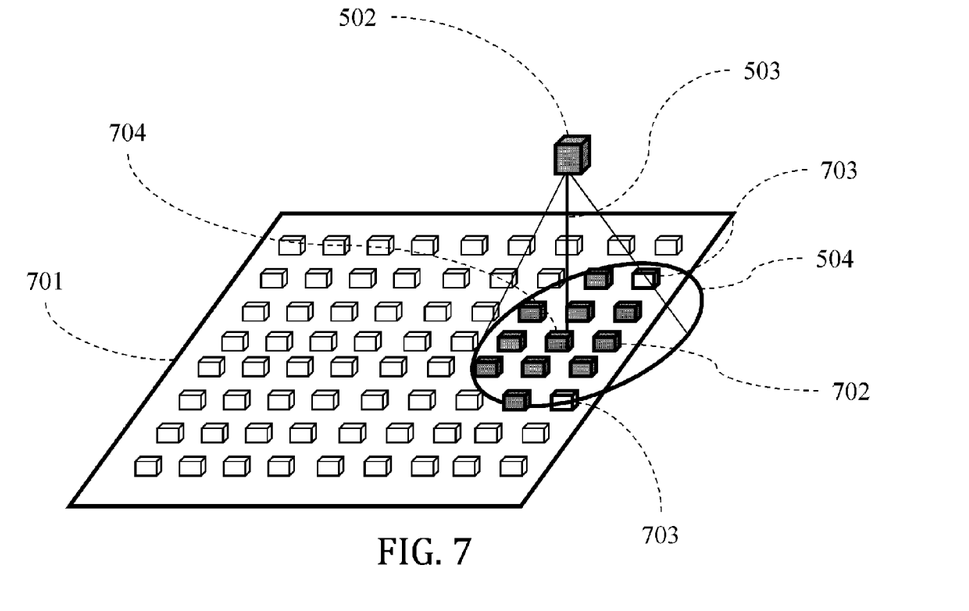
FIG. 7 is a diagram illustrating elements at symmetrical positions in Example 2.

In step S405, the acoustic wave information selection unit 1002 selects virtual elements that are symmetrical with respect to a point of interest, from among effective element selected out of virtual elements on the reception area, and not from among elements on the reception surface. Otherwise, the process is identical to that of Example 1. FIG. 7 illustrates the selection of symmetrical virtual elements.

FIG. 7 illustrates virtual elements 702 that are located at symmetrical positions with respect to a point of interest (voxel) 502, a virtual element 704 in the vicinity of the base of the perpendicular line, and virtual elements 703 at non-symmetrical positions, from among virtual elements on a reception area 701. The virtual element 704 in the vicinity of the base of the perpendicular line, however, can be treated as a virtual element located at a symmetrical position.

In step S406, there are extracted acoustic signals of virtual elements on the reception area, or acoustic signal information being an average value of acoustic signals, on the basis of information on symmetrical elements as selected in a previous step. Otherwise, the process is identical to that of Example 1.

The process in step S407 is identical to that of Example 1, and hence an explanation thereof will be omitted.

In step S408, there is determined whether an unprocessed point of interest is present or not, using, as a reconstruction area, not the area above the reception surface but the area above reception area. Otherwise, the process is identical to that of Example 1.

The processes in step S409 and step S410 are identical to those of Example 1, and hence an explanation thereof will be omitted.

The above procedure allows obtaining a three-dimensional reconstructed image with fewer artifacts, even though the procedure involves an image reconstruction process based on acoustic signals detected at a reception area being an area having a wider reception surface of the acoustic wave detector by moving the acoustic wave detector.

The image information acquiring apparatus described in the above examples can be translated into an image information acquiring method the steps of which are the various processes performed by the respective constituent elements of the image information acquiring apparatus. Also, the present invention can be realized in the form of an image information acquiring program through execution of the various steps of such image information acquiring method as controlled by a program that is run in an information processing device. A computer-readable storage medium in which such image information acquiring program is stored lies also within the scope of the present invention.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2010-164616, filed on Jul. 22, 2010, which is hereby incorporated by reference herein in its entirety.

The invention claimed is:

1. An object information acquiring apparatus, comprising:
   a light source;
   an acoustic wave detector having an array of elements, each element configured to generate an acoustic signal based on a received photoacoustic wave induced by irradiation of an object with light from said light source;
   a reconstructor configured to generate image data for a point of interest of the object from acoustic signals, from elements symmetrically positioned with respect to each other relative to a point within an area of said array, while omitting from generation of the image data an acoustic signal from an element that lies within said area but that has no symmetrically-positioned element within said area, said point in said area being a point within said array where a line perpendicular to the array and extending from said point of interest intersects said array; and
   a position controller configured to move the position of said acoustic wave detector,
   wherein said reconstructor is further configured to generate the image data for the point of interest using acoustic signals from elements in a virtual reception area comprising elements of said acoustic wave detector at different positions, and
   wherein said reconstructor is further configured to generate the image data using acoustic signals from symmetrically positioned elements within said virtual reception area with respect to a point where a line perpendicular to said array and extending from said point of interest intersects said virtual reception area, and
   wherein said position controller is configured to move said acoustic wave detector in such a manner that a part of said array at a position to which said acoustic wave detector is moved overlaps with a part of said array at another position of said acoustic wave detector, and
   in a case where an element used for generation of the image data for the point of interest is included in an overlapping portion of said array, an average of acoustic signals based on the photoacoustic waves detected by the elements at said overlapping portion is determined as an acoustic signal of said element used for generating the image data for the point of interest.

2. The object information acquiring apparatus according to claim 1, wherein said area is substantially circular or square in shape with the center of said area being said point at which said line intersects said array.

3. An object information acquiring method, comprising the steps of:
   irradiating an object with light;
   detecting photoacoustic waves generated by the object at different positions, by moving an acoustic wave detector having an array of elements;
   generating an acoustic signal based on an photoacoustic wave detected by an element of the acoustic wave detector in said detecting step; and generating image data for a point of interest of the object from acoustic signals, from elements symmetrically positioned with respect to each other relative to a point within an area of said array, while an acoustic signal from an element that lies within the area but that has no symmetrically-positioned element within the area is omitted, the point in the area being a point where a line perpendicular to the array and extending from the point of interest intersects the array, wherein the image data for the point of interest is generated using acoustic signals from elements in a virtual reception area comprising elements of said acoustic wave detector at the different positions, and wherein the image data is generated using acoustic signals from symmetrically positioned elements within said virtual reception area with respect to a point where a line perpendicular to said array and extending from said point of interest intersects said virtual reception area, and wherein said acoustic wave detector is moved in such a manner that a part of said array at a position to which said acoustic wave detector is moved overlaps with a part of said array at another position of said acoustic wave detector, and in a case where an element used for generation of the image data for the point of interest is included in an overlapping portion of said array, an average of acoustic signals based on the photoacoustic waves detected by the elements at said overlapping portion is determined as an acoustic signal of said element used for generating the image data for the point of interest.

4. A non-transitory, computer-readable storage medium storing, in executable form, an object information acquiring program for causing an information processing device to execute an image information acquiring method that includes the steps of:

irradiating an object with light;

detecting photoacoustic waves generated by the object at different positions, by moving an acoustic wave detector having an array of elements;

generating an acoustic signal based on a photoacoustic wave detected by an element of the acoustic wave detector in said detecting step; and generating image data for a point of interest of the object from acoustic signals, from elements symmetrically positioned with respect to each other relative to a point within an area of the array, while an acoustic signal from an element that lies within the area but that has no symmetrically-positioned element within the area is omitted from generation of the image data, the point in the area being a point where a line perpendicular to the array and extending from the point of interest intersects the array, wherein the image data for the point of interest is generated using acoustic signals from elements in a virtual reception area comprising elements of said acoustic wave detector at the different positions, and wherein the image data is generated using acoustic signals from symmetrically positioned elements within said virtual reception area with respect to a point where a line perpendicular to said array and extending from said point of interest intersects said virtual reception area, and wherein said acoustic wave detector is moved in such a manner that a part of said array at a position to which said acoustic wave detector is moved overlaps with a part of said array at another position of said acoustic wave detector, and in a case where an element used for generation of the image data for the point of interest is included in an overlapping portion of said array, an average of acoustic signals based on the photoacoustic waves detected by the elements at said overlapping portion is determined as an acoustic signal of said element used for generating the image data for the point of interest.

5. The object information acquiring apparatus according to claim 1, further comprising a selector configured to select said acoustic signals to be used for an image reconstruction for the point of interest of the object from said array.

6. The object information acquiring apparatus according to claim 5, wherein said selector is further configured to select, as a signal used for image reconstruction, an acoustic signal generated by an element located at a position at which said line intersects said array.

7. The object information acquiring apparatus according to claim 5, wherein said selector selects a particular signal on the basis of the position of an element from which that signal is generated and said point of interest, and on the basis of the directionality of said elements, such that the selected signal is at a predetermined effective level.

8. The object information acquiring apparatus according to claim 1, wherein said elements of said array of elements are arranged two-dimensionally.

* * * * *